United States Patent
Voss

(10) Patent No.: US 9,889,276 B2
(45) Date of Patent: Feb. 13, 2018

(54) SYSTEMS FOR ANCHORING A MEDICAL DEVICE IN A BODY LUMEN

(71) Applicant: Abbott Laboratories, Redwood City, CA (US)

(72) Inventor: Laveille Kao Voss, Belmont, CA (US)

(73) Assignee: ABBOTT LABORATORIES, Abbott Park, IL (US)

( * ) Notice: Subject to any disclaimer, the term of this patent is extended or adjusted under 35 U.S.C. 154(b) by 290 days.

(21) Appl. No.: 14/674,756

(22) Filed: Mar. 31, 2015

(65) Prior Publication Data

US 2015/0273186 A1 Oct. 1, 2015

Related U.S. Application Data

(60) Continuation of application No. 13/525,875, filed on Jun. 18, 2012, now Pat. No. 8,998,932, which is a
(Continued)

(51) Int. Cl.
*A61B 17/10* (2006.01)
*A61M 25/04* (2006.01)
(Continued)

(52) U.S. Cl.
CPC .......... *A61M 25/04* (2013.01); *A61B 17/0057* (2013.01); *A61B 17/3417* (2013.01); *A61B 17/3421* (2013.01); *A61F 2/064* (2013.01); *A61B 2017/00592* (2013.01); *A61B 2017/00637* (2013.01); *A61B 2017/00659* (2013.01); *A61B 2017/00663* (2013.01); *A61B 2017/00672* (2013.01); *A61B 2017/00867* (2013.01); *A61B 2017/047* (2013.01);
(Continued)

(58) Field of Classification Search
CPC ... A61B 17/04; A61B 17/062; A61B 17/0057; A61B 2017/00663; A61B 2017/00575; A61B 2017/00623; A61B 17/0469; A61B 17/0482; A61B 2017/00637
See application file for complete search history.

(56) References Cited

U.S. PATENT DOCUMENTS

| 312,408 A | 2/1885 | Wackerhagen |
| 597,165 A | 1/1898 | Hall |

(Continued)

FOREIGN PATENT DOCUMENTS

| DE | 912619 | 5/1954 |
| DE | 4210724 | 7/1993 |

(Continued)

OTHER PUBLICATIONS

US 5,820,544, 06/1974, Semm (withdrawn)
(Continued)

*Primary Examiner* — Tuan V Nguyen
(74) *Attorney, Agent, or Firm* — Workman Nydegger; Randy Shen

(57) ABSTRACT

A system for securing a device in tissue, having a sheath having a plurality of side openings; a rotatable element disposed within the sheath; and a plurality of curved projections extending from the rotatable element, wherein rotation of the rotatable element within the sheath pushes distal ends of each of the curved projections outwardly through one of the plurality of openings and into the tissue.

21 Claims, 11 Drawing Sheets

Related U.S. Application Data continuation of application No. 12/955,869, filed on Nov. 29, 2010, now Pat. No. 8,202,281, which is a continuation of application No. 11/552,593, filed on Oct. 25, 2006, now Pat. No. 7,842,049, which is a division of application No. 10/335,147, filed on Dec. 31, 2002, now Pat. No. 7,160,309.

(51) Int. Cl.
  *A61B 17/00* (2006.01)
  *A61B 17/34* (2006.01)
  *A61F 2/06* (2013.01)
  *A61B 17/04* (2006.01)

(52) U.S. Cl.
  CPC ............. *A61B 2017/0472* (2013.01); *A61B 2017/3484* (2013.01); *A61B 2017/3488* (2013.01)

(56) References Cited

U.S. PATENT DOCUMENTS

| | | |
|---|---|---|
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,580,566 A | 4/1986 | Hsu |
| 4,586,614 A | 5/1986 | Ger |
| 4,587,969 A | 5/1986 | Gillis |
| 4,596,559 A | 6/1986 | Fleishhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,823,794 A | 4/1989 | Pierce |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yo On |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |

(56) References Cited

U.S. PATENT DOCUMENTS

| | | |
|---|---|---|
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evansetal |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,407 A | 11/1994 | Poll |
| 5,364,408 A | 11/1994 | Gordon |
| 5,368,595 A | 11/1994 | Lewis |
| 5,368,601 A * | 11/1994 | Sauer .............. A61B 17/0469 112/169 |
| 5,374,275 A | 12/1994 | Bradley et al. |
| 5,374,278 A | 12/1994 | Chesterfield et al. |
| 5,376,096 A | 12/1994 | Foster |
| 5,383,896 A | 1/1995 | Gershony et al. |
| 5,383,905 A | 1/1995 | Golds et al. |
| 5,385,569 A | 1/1995 | Swor |
| 5,387,221 A | 2/1995 | Bisgaard |
| 5,387,227 A | 2/1995 | Grice |
| 5,391,176 A | 2/1995 | de la Torre |
| 5,391,182 A | 2/1995 | Chin |
| 5,395,332 A | 3/1995 | Ressemann et al. |
| 5,395,349 A | 3/1995 | Quiachon et al. |
| 5,397,310 A | 3/1995 | Chu et al. |
| 5,397,325 A | 3/1995 | Delia Badia et al. |
| 5,397,326 A | 3/1995 | Mangum |
| 5,403,329 A | 4/1995 | Hinchcliffe |
| 5,403,331 A | 4/1995 | Chesterfield et al. |
| 5,403,338 A | 4/1995 | Milo |
| 5,405,352 A | 4/1995 | Weston |
| 5,411,481 A | 5/1995 | Allen et al. |
| 5,413,571 A | 5/1995 | Katsaros et al. |
| 5,417,684 A | 5/1995 | Jackson et al. |
| 5,417,699 A | 5/1995 | Klein et al. |
| 5,419,765 A | 5/1995 | Weldon et al. |
| 5,425,705 A | 6/1995 | Evard et al. |
| 5,425,737 A | 6/1995 | Burbank et al. |
| 5,425,740 A | 6/1995 | Hutchinson, Jr. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schob et al. |
| 5,454,834 A | 10/1995 | Boebel et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,464,426 A | 11/1995 | Bonutti |
| 5,466,241 A | 11/1995 | Leroy et al. |
| 5,470,338 A | 11/1995 | Whitfield et al. |
| 5,474,568 A | 12/1995 | Scott |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,655 A | 5/1996 | Davila et al. |
| 5,520,665 A | 5/1996 | Fleetwood |
| 5,520,691 A | 5/1996 | Branch |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Hartnett |
| 5,531,700 A | 7/1996 | Moore et al. |
| 5,536,273 A | 7/1996 | Lehrer |
| 5,540,701 A | 7/1996 | Sharkey et al. |
| 5,540,703 A | 7/1996 | Barker, Jr. et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,549,631 A | 8/1996 | Bonutti |
| 5,554,162 A | 9/1996 | DeLange |
| 5,562,684 A | 10/1996 | Kammerer |
| 5,562,686 A | 10/1996 | Sauer et al. |
| 5,562,688 A | 10/1996 | Riza |
| 5,562,728 A | 10/1996 | Lazarus et al. |
| 5,567,435 A | 10/1996 | Hubbell et al. |
| 5,569,269 A | 10/1996 | Hart et al. |
| 5,569,271 A | 10/1996 | Hoel |
| 5,571,120 A | 11/1996 | Yoon |
| 5,573,540 A | 11/1996 | Yoon |
| 5,584,842 A | 12/1996 | Fogarty et al. |
| 5,591,177 A | 1/1997 | Lehrer |
| 5,591,179 A | 1/1997 | Edelstein |
| 5,591,206 A | 1/1997 | Moufarrege |
| 5,593,421 A | 1/1997 | Bauer |
| 5,601,572 A | 2/1997 | Middleman et al. |
| 5,603,718 A | 2/1997 | Xu |
| 5,607,435 A | 3/1997 | Sachdeva et al. |
| 5,609,597 A | 3/1997 | Lehrer |
| 5,611,794 A | 3/1997 | Sauer et al. |
| 5,613,974 A | 3/1997 | Andreas et al. |
| 5,613,975 A | 3/1997 | Christy |
| 5,624,446 A | 4/1997 | Harryman, II |
| 5,626,588 A | 5/1997 | Sauer et al. |
| 5,643,289 A | 7/1997 | Sauer et al. |
| 5,643,295 A | 7/1997 | Yoon |
| 5,643,318 A | 7/1997 | Tsukernik et al. |
| 5,649,959 A | 7/1997 | Hannam et al. |
| 5,662,664 A | 9/1997 | Gordon et al. |
| 5,669,917 A | 9/1997 | Sauer et al. |
| 5,676,689 A | 10/1997 | Kensey et al. |
| 5,700,273 A | 12/1997 | Buelna et al. |
| 5,707,379 A | 1/1998 | Fleenor et al. |
| 5,713,910 A | 2/1998 | Gordon et al. |

(56) References Cited

U.S. PATENT DOCUMENTS

| | | |
|---|---|---|
| 5,716,369 A | 2/1998 | Riza |
| 5,720,574 A | 2/1998 | Barella |
| 5,720,757 A | 2/1998 | Hathaway et al. |
| 5,722,981 A | 3/1998 | Stevens |
| 5,725,552 A | 3/1998 | Kotula et al. |
| 5,728,109 A | 3/1998 | Schulze et al. |
| 5,728,114 A | 3/1998 | Evans et al. |
| 5,728,133 A | 3/1998 | Kontos |
| 5,728,151 A | 3/1998 | Garrison et al. |
| 5,741,276 A | 4/1998 | Poloyko et al. |
| 5,741,280 A | 4/1998 | Fleenor |
| 5,746,755 A | 5/1998 | Wood et al. |
| 5,749,890 A | 5/1998 | Shaknovich |
| 5,755,727 A | 5/1998 | Kontos |
| 5,759,188 A | 6/1998 | Yoon |
| 5,766,183 A | 6/1998 | Sauer |
| 5,766,186 A | 6/1998 | Faraz et al. |
| 5,766,217 A | 6/1998 | Christy |
| 5,769,862 A | 6/1998 | Kammerer et al. |
| 5,779,719 A | 7/1998 | Klein et al. |
| 5,782,860 A | 7/1998 | Epstein et al. |
| 5,782,861 A | 7/1998 | Cragg et al. |
| 5,792,151 A | 8/1998 | Heck et al. |
| 5,792,152 A | 8/1998 | Klein et al. |
| 5,797,928 A | 8/1998 | Kogasaka |
| 5,797,929 A | 8/1998 | Andreas et al. |
| 5,799,661 A | 9/1998 | Boyd et al. |
| 5,810,849 A | 9/1998 | Kontos |
| 5,810,850 A | 9/1998 | Hathaway et al. |
| 5,810,884 A | 9/1998 | Kim |
| 5,814,069 A | 9/1998 | Schulze et al. |
| 5,817,113 A | 10/1998 | Gifford, III et al. |
| 5,820,631 A | 10/1998 | Nobles |
| 5,824,010 A | 10/1998 | McDonald |
| 5,824,111 A | 10/1998 | Schall et al. |
| 5,830,125 A | 11/1998 | Scribner et al. |
| 5,836,955 A | 11/1998 | Buelna et al. |
| 5,836,956 A | 11/1998 | Buelna et al. |
| 5,846,253 A | 12/1998 | Buelna et al. |
| 5,848,714 A | 12/1998 | Robson et al. |
| 5,855,585 A | 1/1999 | Kontos |
| 5,860,963 A | 1/1999 | Azam et al. |
| 5,860,990 A | 1/1999 | Nobles et al. |
| 5,860,991 A | 1/1999 | Klein et al. |
| 5,861,005 A | 1/1999 | Kontos |
| 5,871,490 A | 2/1999 | Schulze et al. |
| 5,871,502 A | 2/1999 | Suryadevara |
| 5,873,876 A | 2/1999 | Christy |
| 5,876,411 A | 3/1999 | Kontos |
| 5,895,404 A | 4/1999 | Ruiz |
| 5,897,487 A | 4/1999 | Ouchi |
| 5,897,564 A | 4/1999 | Schulze et al. |
| 5,902,311 A | 5/1999 | Andreas et al. |
| 5,904,597 A | 5/1999 | Doi et al. |
| 5,904,690 A | 5/1999 | Middleman et al. |
| 5,904,697 A | 5/1999 | Gifford, III et al. |
| 5,906,631 A | 5/1999 | Imran |
| 5,919,207 A | 7/1999 | Taheri |
| 5,921,994 A | 7/1999 | Andreas et al. |
| 5,928,266 A | 7/1999 | Kontos |
| 5,951,590 A | 9/1999 | Goldfarb |
| 5,954,732 A | 9/1999 | Hart et al. |
| 5,957,936 A | 9/1999 | Yoon et al. |
| 5,957,937 A | 9/1999 | Yoon |
| 5,957,938 A | 9/1999 | Zhu et al. |
| 5,964,773 A * | 10/1999 | Greenstein ......... A61B 17/0469 606/144 |
| 5,964,782 A | 10/1999 | Lafontaine et al. |
| 5,972,030 A | 10/1999 | Garrison et al. |
| 5,976,161 A | 11/1999 | Kirsch et al. |
| 5,980,539 A | 11/1999 | Kontos |
| 5,997,555 A | 12/1999 | Kontos |
| 6,001,109 A | 12/1999 | Kontos |
| 6,022,372 A | 2/2000 | Kontos |
| 6,024,747 A | 2/2000 | Kontos |
| 6,036,699 A | 3/2000 | Andreas et al. |
| 6,042,601 A | 3/2000 | Smith |
| 6,048,351 A | 4/2000 | Gordon et al. |
| 6,048,354 A | 4/2000 | Lawrence |
| 6,048,357 A | 4/2000 | Kontos |
| 6,059,800 A | 5/2000 | Hart et al. |
| 6,068,603 A | 5/2000 | Suzuki |
| 6,077,276 A | 6/2000 | Kontos |
| 6,077,279 A | 6/2000 | Kontos |
| 6,117,144 A * | 9/2000 | Nobles ............... A61B 17/0057 606/139 |
| 6,117,145 A | 9/2000 | Wood et al. |
| 6,126,675 A | 10/2000 | Shchervinsky et al. |
| 6,132,439 A | 10/2000 | Kontos |
| 6,132,440 A | 10/2000 | Hathaway et al. |
| 6,136,010 A | 10/2000 | Modesitt et al. |
| 6,139,556 A | 10/2000 | Kontos |
| 6,152,936 A | 11/2000 | Christy et al. |
| 6,165,183 A | 12/2000 | Kuehn et al. |
| 6,165,204 A | 12/2000 | Levinson et al. |
| 6,190,396 B1 | 2/2001 | Whitin et al. |
| 6,197,042 B1 | 3/2001 | Ginn et al. |
| 6,206,893 B1 | 3/2001 | Klein et al. |
| 6,206,895 B1 | 3/2001 | Levinson |
| 6,245,079 B1 | 6/2001 | Nobles et al. |
| 6,248,124 B1 | 6/2001 | Pedros et al. |
| 6,296,657 B1 | 10/2001 | Brucker |
| 6,302,870 B1 | 10/2001 | Jacobsen et al. |
| 6,348,059 B1 | 2/2002 | Hathaway et al. |
| 6,355,050 B1 | 3/2002 | Andreas et al. |
| 6,358,258 B1 | 3/2002 | Arcia et al. |
| 6,395,015 B1 | 5/2002 | Borst et al. |
| 6,428,472 B1 | 8/2002 | Haas |
| 6,428,549 B1 | 8/2002 | Kontos |
| 6,436,109 B1 | 8/2002 | Kontos |
| 6,443,963 B1 | 9/2002 | Baldwin et al. |
| 6,451,031 B1 | 9/2002 | Kontos |
| 6,511,489 B2 | 1/2003 | Field et al. |
| 6,517,553 B2 | 2/2003 | Klein et al. |
| 6,533,812 B2 | 3/2003 | Swanson et al. |
| 6,551,330 B1 | 4/2003 | Bain et al. |
| 6,558,399 B1 | 5/2003 | Isbell et al. |
| 6,562,052 B2 | 5/2003 | Nobles et al. |
| 6,569,185 B2 | 5/2003 | Ungs |
| 6,572,629 B2 | 6/2003 | Kalloo et al. |
| 6,610,072 B1 | 8/2003 | Christy et al. |
| 6,623,509 B2 | 9/2003 | Ginn |
| 6,623,510 B2 | 9/2003 | Carley et al. |
| 6,632,237 B2 | 10/2003 | Ben-David et al. |
| 6,641,592 B1 | 11/2003 | Sauer et al. |
| 6,663,655 B2 | 12/2003 | Ginn et al. |
| 6,676,685 B2 | 1/2004 | Pedros et al. |
| 6,695,867 B2 | 2/2004 | Ginn et al. |
| 6,716,228 B2 | 4/2004 | Tal |
| 6,743,195 B2 | 6/2004 | Zucker |
| 6,743,259 B2 | 6/2004 | Ginn |
| 6,749,621 B2 | 6/2004 | Pantages et al. |
| 6,749,622 B2 | 6/2004 | McGuckin, Jr. et al. |
| 6,837,906 B2 | 1/2005 | Ginn |
| 6,846,319 B2 | 1/2005 | Ginn et al. |
| 6,890,343 B2 | 5/2005 | Ginn et al. |
| 6,896,692 B2 | 5/2005 | Ginn et al. |
| 6,911,034 B2 | 6/2005 | Nobles et al. |
| 6,939,357 B2 | 9/2005 | Navarro et al. |
| 6,964,668 B2 | 11/2005 | Modesitt et al. |
| 6,969,371 B2 | 11/2005 | Palasis et al. |
| 6,969,397 B2 | 11/2005 | Ginn |
| 7,001,400 B1 | 2/2006 | Modesitt et al. |
| 7,029,480 B2 | 4/2006 | Klein et al. |
| 7,029,481 B1 | 4/2006 | Burdulis, Jr. et al. |
| 7,048,747 B2 | 5/2006 | Arcia et al. |
| 7,063,710 B2 | 6/2006 | Takamoto et al. |
| 7,083,635 B2 | 8/2006 | Ginn |
| 7,108,710 B2 | 9/2006 | Anderson |
| 7,112,225 B2 | 9/2006 | Ginn |
| 7,131,980 B1 | 11/2006 | Field et al. |
| 7,160,309 B2 | 1/2007 | Voss |
| 7,179,266 B2 | 2/2007 | Kontos |
| 7,229,458 B2 | 6/2007 | Boecker et al. |

(56) References Cited

U.S. PATENT DOCUMENTS

| | | |
|---|---|---|
| 7,235,087 B2 | 6/2007 | Modesitt et al. |
| 7,316,704 B2 | 1/2008 | Bagaoisan et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| 7,361,183 B2 | 4/2008 | Ginn |
| 7,361,185 B2 | 4/2008 | O'Malley et al. |
| 7,377,927 B2 | 5/2008 | Burdulis, Jr. et al. |
| 7,390,328 B2 | 6/2008 | Modesitt |
| 7,393,363 B2 | 7/2008 | Ginn |
| 7,442,198 B2 | 10/2008 | Gellman et al. |
| 7,445,626 B2 | 11/2008 | Songer et al. |
| 7,449,024 B2 | 11/2008 | Stafford |
| 7,462,188 B2 | 12/2008 | McIntosh |
| 7,753,923 B2 | 7/2010 | St. Goar et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,842,049 B2 | 11/2010 | Voss |
| 7,846,170 B2 | 12/2010 | Modesitt et al. |
| 7,850,701 B2 | 12/2010 | Modesitt |
| 7,883,517 B2 | 2/2011 | Pantages et al. |
| 8,038,688 B2 | 10/2011 | Modesitt et al. |
| 8,048,092 B2 | 11/2011 | Modesitt et al. |
| 8,057,491 B2 | 11/2011 | Modesitt et al. |
| 8,083,754 B2 | 12/2011 | Pantages et al. |
| 8,137,364 B2 | 3/2012 | Zung et al. |
| 8,172,860 B2 | 5/2012 | Zung et al. |
| 8,202,281 B2 | 6/2012 | Voss |
| 8,211,122 B2 | 7/2012 | McIntosh |
| 8,252,008 B2 | 8/2012 | Ma |
| 8,257,368 B2 | 9/2012 | McIntosh |
| 8,267,947 B2 | 9/2012 | Pantages et al. |
| 8,313,498 B2 | 11/2012 | Pantages et al. |
| 8,323,298 B2 | 12/2012 | Modesitt et al. |
| 8,361,088 B2 | 1/2013 | McIntosh |
| 8,419,753 B2 | 4/2013 | Stafford |
| 8,430,893 B2 | 4/2013 | Ma |
| 8,512,375 B2 | 8/2013 | Torrie et al. |
| 8,574,244 B2 | 11/2013 | Reynolds |
| 8,597,309 B2 | 12/2013 | Stafford |
| 8,663,248 B2 | 3/2014 | Zung et al. |
| 8,663,252 B2 | 3/2014 | Fortson |
| 8,858,573 B2 | 10/2014 | Fortson et al. |
| 8,864,778 B2 | 10/2014 | Fortson et al. |
| 8,998,932 B2 * | 4/2015 | Voss .................. A61B 17/0057 606/139 |
| 2001/0046518 A1 | 11/2001 | Sawhney |
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2003/0093093 A1 | 5/2003 | Modesitt et al. |
| 2003/0171764 A1 | 9/2003 | Debbas |
| 2003/0195529 A1 | 10/2003 | Takamoto et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1 | 9/2004 | Zarbatany et al. |
| 2004/0186487 A1 | 9/2004 | Klein et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0069397 A1 | 3/2006 | Nobles et al. |
| 2006/0100664 A1 | 5/2006 | Pai et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2007/0005079 A1 | 1/2007 | Zarbatany et al. |
| 2007/0032801 A1 | 2/2007 | Pantages et al. |
| 2007/0060950 A1 | 3/2007 | Khosravi et al. |
| 2007/0123817 A1 | 5/2007 | Khosravi et al. |
| 2007/0282354 A1 | 12/2007 | McIntosh |
| 2008/0009794 A1 | 1/2008 | Bagaoisan et al. |
| 2008/0065151 A1 | 3/2008 | Ginn |
| 2008/0065152 A1 | 3/2008 | Carley |
| 2008/0287967 A1 | 11/2008 | Andreas et al. |
| 2011/0071567 A1 | 3/2011 | Modesitt et al. |
| 2011/0077670 A1 | 3/2011 | Modesitt et al. |
| 2011/0190793 A1 | 8/2011 | Nobles et al. |
| 2011/0288563 A1 | 11/2011 | Gianotti et al. |
| 2012/0016383 A1 | 1/2012 | Sauer et al. |
| 2012/0150201 A1 | 6/2012 | Pantages et al. |
| 2012/0283749 A1 | 11/2012 | Sauer |
| 2013/0012962 A1 | 1/2013 | Stone |
| 2013/0066340 A1 | 3/2013 | Pantages et al. |
| 2013/0138122 A1 | 5/2013 | McIntosh |
| 2013/0190781 A1 | 7/2013 | Fortson et al. |
| 2013/0237999 A1 | 9/2013 | Ma |
| 2013/0325058 A1 | 12/2013 | Roorda et al. |
| 2014/0180312 A1 | 6/2014 | Zung et al. |
| 2014/0222032 A1 | 8/2014 | Stafford |
| 2014/0236189 A1 | 8/2014 | Melsheimer et al. |
| 2015/0025551 A1 | 1/2015 | Fortson et al. |
| 2015/0119906 A1 | 4/2015 | Bagaoisan et al. |
| 2016/0135803 A1 | 5/2016 | McIntosh |
| 2016/0192914 A1 | 7/2016 | Ma |
| 2016/0287229 A1 | 10/2016 | Zung et al. |

FOREIGN PATENT DOCUMENTS

| | | |
|---|---|---|
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |

(56) References Cited

FOREIGN PATENT DOCUMENTS

| | | |
|---|---|---|
| SU | 1648400 | 5/1991 |
| WO | WO 85/03858 | 9/1985 |
| WO | WO 01/35833 | 2/1994 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 02/036021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 05/000126 | 1/2005 |
| WO | WO 05/023119 | 3/2005 |
| WO | WO 05/025430 | 3/2005 |
| WO | WO 05/030060 | 4/2005 |
| WO | WO 05/041782 | 5/2005 |
| WO | WO 05/063129 | 7/2005 |
| WO | WO 05/065549 | 7/2005 |
| WO | WO 05/092204 | 10/2005 |
| WO | WO 05/112782 | 12/2005 |
| WO | WO 06/026116 | 3/2006 |
| WO | WO 06/052611 | 5/2006 |
| WO | WO 06/052612 | 5/2006 |
| WO | WO 06/078578 | 7/2006 |
| WO | WO 06/115901 | 11/2006 |
| WO | WO 06/115904 | 11/2006 |
| WO | WO 06/118877 | 11/2006 |
| WO | WO 07/019016 | 2/2007 |
| WO | WO 07/081836 | 7/2007 |

OTHER PUBLICATIONS

U.S. Appl. No. 15/186,730, filed Jun. 20, 2016, Fortson et al.
U.S. Appl. No. 15/192,481, filed Jun. 24, 2016, Stafford.
U.S. Appl. No. 13/333,411, dated Apr. 4, 2016, Office Action.
U.S. Appl. No. 13/485,388, dated Oct. 7, 2015, Notice of Allowance.
U.S. Appl. No. 13/615,523, dated Feb. 26, 2016, Office Action.
U.S. Appl. No. 13/615,523, dated Aug. 18, 2016, Office Action.
U.S. Appl. No. 13/791,858, dated Nov. 10, 2015, Office Action.
U.S. Appl. No. 13/791,858, dated Mar. 15, 2016, Notice of Allowance.
U.S. Appl. No. 13/870,628, dated Nov. 12, 2015, Notice of Allowance.
U.S. Appl. No. 14/094,352, dated Mar. 22, 2016, Notice of Allowance.
U.S. Appl. No. 14/195,308, dated Aug. 11, 2015, Office Action.
U.S. Appl. No. 14/195,308, dated Dec. 4, 2015, Notice of Allowance.
U.S. Appl. No. 15/434,907, filed Feb. 16, 2017, Aaron M. Fortson.
U.S. Appl. No. 13/615,523, dated Nov. 30, 2016, Notice of Allowance.
U.S. Appl. No. 14/511,730, dated Jan. 20, 2017, Office Action.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt, et al.
Cardiac Catheterization and Angiography, 3rd Ed., Lea & Febiger, Philadelphia, pp. 1-49, 52-247. 1986.
Cardio-Thoracic Systems Prospectus dated Mar. 20, 1996. pp. 1-4, 25-40.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques For Palmaz-Schatz Stent Deployment In Lesions With A Large Side Branch, Catheterization and Cardiovascular Diagnosis, 34: 353-361, 1995.
Definition of "pair", Dictionary.com, accessed on May 5, 2014.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintcchnik GmbH, Product Brochure entitled "REMA," Apr. 2001, 7 pages.
Serruys, PW et al., A Comparision of Balloon-Expandable-Stent Implantation With Balloon Angioplasty In Patients With Coronary Artery Disease, New England Journal of Medicine, 331:489-495, 1994.
Taber's Cyclopedic Medical Dictionary, 18th Ed., p. 747, Feb. 1997.
U.S. Appl. No. 07/989,611, dated May 12, 1993, Office Action.
U.S. Appl. No. 07/989,611, dated Aug. 1, 1994, Office Action.
U.S. Appl. No. 07/989,611, dated Nov. 3, 1994, Notice of Allowance.
U.S. Appl. No. 08/148,809, dated Sep. 16, 1994, Office Action.
U.S. Appl. No. 08/148,809, dated May 30, 1995, Office Action.
U.S. Appl. No. 08/148,809, dated Dec. 15, 1995, Notice of Allowance.
U.S. Appl. No. 08/252,124, dated Jun. 5, 1995, Office Action.
U.S. Appl. No. 08/252,124, dated Jan. 5, 1996, Office Action.
U.S. Appl. No. 08/252,124, dated May 22, 1996, Notice of Allowance.
U.S. Appl. No. 08/259,410, dated Feb. 2, 1995, Office Action.
U.S. Appl. No. 08/259,410, dated Jun. 1, 1995, Office Action.
U.S. Appl. No. 08/259,410, dated Feb. 6, 1998, Notice of Allowance.
U.S. Appl. No. 08/638,076, dated Jan. 21, 1997, Office Action.
U.S. Appl. No. 08/638,076, dated Oct. 17, 1997, Notice of Allowance.
U.S. Appl. No. 08/824,031, dated Mar. 16, 1998, Office Action.
U.S. Appl. No. 08/824,031, dated Sep. 14, 1998, Office Action.
U.S. Appl. No. 08/824,031, dated Apr. 13, 1999, Office Action.
U.S. Appl. No. 08/824,031, dated Jul. 15, 1999, Notice of Allowance.
U.S. Appl. No. 08/883,246, dated Jul. 23, 1998, Office Action.
U.S. Appl. No. 08/883,246, dated Apr. 12, 1999, Office Action.
U.S. Appl. No. 08/883,246, dated Oct. 13, 1999, Office Action.
U.S. Appl. No. 08/883,246, dated Oct. 23, 2000, Office Action.
U.S. Appl. No. 08/883,246, dated Jul. 11, 2001, Office Action.
U.S. Appl. No. 08/883,246, dated Sep. 11, 2001, Notice of Allowance.
U.S. Appl. No. 09/057,108, dated Jul. 10, 2000, Office Action.
U.S. Appl. No. 09/057,108, dated Oct. 25, 2000, Notice of Allowance.
U.S. Appl. No. 09/262,402, dated Mar. 29, 2000, Office Action.
U.S. Appl. No. 09/262,402, dated May 30, 2000, Notice of Allowance.
U.S. Appl. No. 09/395,901, dated Jun. 27, 2000, Office Action.

(56) References Cited

OTHER PUBLICATIONS

U.S. Appl. No. 09/395,901, dated Nov. 6, 2000, Office Action.
U.S. Appl. No. 09/395,901, dated Apr. 20, 2001, Notice of Allowance.
U.S. Appl. No. 09/395,901, dated Sep. 10, 2001, Notice of Allowance.
U.S. Appl. No. 09/610,099, dated Jul. 11, 2002, Office Action.
U.S. Appl. No. 09/610,099, dated Dec. 24, 2002, Notice of Allowance.
U.S. Appl. No. 09/651,344, dated Feb. 28, 2003, Office Action.
U.S. Appl. No. 09/651,344, dated Nov. 7, 2003, Office Action.
U.S. Appl. No. 09/651,344, dated Apr. 20, 2004, Notice of Allowance.
U.S. Appl. No. 09/707,746, dated Feb. 16, 2005, Office Action.
U.S. Appl. No. 09/707,746, dated Jul. 7, 2005, Office Action.
U.S. Appl. No. 09/707,746, dated Nov. 15, 2005, Notice of Allowance.
U.S. Appl. No. 09/769,109, dated Oct. 23, 2001, Office Action.
U.S. Appl. No. 09/769,109, dated Jun. 17, 2002, Office Action.
U.S. Appl. No. 09/769,109, dated Sep. 9, 2002, Notice of Allowance.
U.S. Appl. No. 09/988,541, dated Mar. 17, 2004, Office Action.
U.S. Appl. No. 09/988,541, dated Feb. 28, 2005, Office Action.
U.S. Appl. No. 09/988,541, dated May 25, 2005, Office Action.
U.S. Appl. No. 09/988,541, dated Aug. 24, 2005, Office Action.
U.S. Appl. No. 09/988,541, dated Nov. 8, 2005, Office Action.
U.S. Appl. No. 09/988,541, dated Dec. 13, 2005, Notice of Allowance.
U.S. Appl. No. 10/033,689, dated Sep. 30, 2003, Office Action.
U.S. Appl. No. 10/152,272, dated Jan. 24, 2005, Office Action.
U.S. Appl. No. 10/152,272, dated May 13, 2005, Notice of Allowance.
U.S. Appl. No. 10/335,065, dated Mar. 17, 2005, Office Action.
U.S. Appl. No. 10/335,065, dated Jun. 10, 2005, Office Action.
U.S. Appl. No. 10/335,065, dated Nov. 17, 2005, Notice of Allowance.
U.S. Appl. No. 10/335,147, dated Dec. 13, 2005, Office Action.
U.S. Appl. No. 10/335,147, dated Apr. 17, 2006, Office Action.
U.S. Appl. No. 10/335,147, dated Oct. 4, 2006, Notice of Allowance.
U.S. Appl. No. 10/357,984, dated Jan. 9, 2006, Office Action.
U.S. Appl. No. 10/357,984, dated Mar. 16, 2006, Office Action.
U.S. Appl. No. 10/357,984, dated Sep. 28, 2006, Office Action.
U.S. Appl. No. 10/357,984, dated Mar. 23, 2007, Office Action.
U.S. Appl. No. 10/357,984, dated Nov. 14, 2007, Office Action.
U.S. Appl. No. 10/652,182, dated Aug. 9, 2006, Office Action.
U.S. Appl. No. 10/652,182, dated Feb. 22, 2007, Notice of Allowance.
U.S. Appl. No. 10/660,288, dated Nov. 15, 2005, Office Action.
U.S. Appl. No. 10/660,288, dated Mar. 9, 2006, Office Action.
U.S. Appl. No. 10/660,288, dated Aug. 24, 2006, Office Action.
U.S. Appl. No. 10/660,288, dated Feb. 1, 2007, Office Action.
U.S. Appl. No. 10/660,288, dated Jun. 28, 2007, Office Action.
U.S. Appl. No. 10/660,288, dated Apr. 29, 2009, Office Action.
U.S. Appl. No. 10/660,288, dated Aug. 3, 2009, Office Action.
U.S. Appl. No. 10/660,288, dated Mar. 30, 2010, Office Action.
U.S. Appl. No. 10/660,288, dated Mar. 29, 2011, Office Action.
U.S. Appl. No. 10/660,288, dated Sep. 30, 2011, Notice of Allowance.
U.S. Appl. No. 10/729,541, dated Dec. 12, 2006, Office Action.
U.S. Appl. No. 10/729,541, dated Jun. 18, 2007, Office Action.
U.S. Appl. No. 10/729,541, dated Jan. 8, 2008, Office Action.
U.S. Appl. No. 10/729,541, dated Sep. 23, 2008, Office Action.
U.S. Appl. No. 10/729,541, dated May 1, 2009, Office Action.
U.S. Appl. No. 10/729,541, dated Nov. 16, 2009, Notice of Allowance.
U.S. Appl. No. 10/729,541, dated Mar. 25, 2010, Notice of Allowance.
U.S. Appl. No. 10/729,541, dated Jul. 12, 2010, Notice of Allowance.
U.S. Appl. No. 10/737,668, dated Nov. 2, 2005, Office Action.
U.S. Appl. No. 10/737,668, dated Feb. 16, 2006, Office Action.
U.S. Appl. No. 10/737,668, dated Oct. 19, 2006, Office Action.
U.S. Appl. No. 10/737,668, dated Jun. 7, 2007, Office Action.
U.S. Appl. No. 10/737,668, dated Nov. 28, 2007, Office Action.
U.S. Appl. No. 10/737,668, dated Jun. 26, 2008, Notice of Allowance.
U.S. Appl. No. 10/742,406, dated Mar. 23, 2007, Office Action.
U.S. Appl. No. 10/742,406, dated Sep. 10, 2007, Notice of Allowance.
U.S. Appl. No. 10/742,406, dated Jan. 11, 2008, Notice of Allowance.
U.S. Appl. No. 10/746,210, dated Apr. 5, 2007, Office Action.
U.S. Appl. No. 10/746,210, dated Aug. 21, 2007, Office Action.
U.S. Appl. No. 10/746,210, dated Jul. 9, 2008, Notice of Allowance.
U.S. Appl. No. 10/813,449, dated Sep. 5, 2006, Office Action.
U.S. Appl. No. 10/813,449, dated Jul. 16, 2007, Office Action.
U.S. Appl. No. 10/813,449, dated Jan. 25, 2008, Office Action.
U.S. Appl. No. 10/813,449, dated Aug. 14, 2008, Office Action.
U.S. Appl. No. 10/813,449, dated Sep. 15, 2008, Office Action.
U.S. Appl. No. 10/813,449, dated Feb. 3, 2009, Office Action.
U.S. Appl. No. 10/813,449, dated Aug. 28, 2009, Office Action.
U.S. Appl. No. 10/813,449, dated May 27, 2010, Office Action.
U.S. Appl. No. 10/909,531, dated Apr. 4, 2007, Office Action.
U.S. Appl. No. 10/909,531, dated Dec. 26, 2007, Office Action.
U.S. Appl. No. 10/909,531, dated Jun. 13, 2008, Office Action.
U.S. Appl. No. 10/909,531, dated Feb. 9, 2009, Office Action.
U.S. Appl. No. 10/909,531, dated Sep. 16, 2009, Office Action.
U.S. Appl. No. 10/909,531, dated Apr. 29, 2010, Notice of Allowance.
U.S. Appl. No. 10/909,531, dated Aug. 20, 2010, Notice of Allowance.
U.S. Appl. No. 10/948,445, dated Jul. 11, 2007, Office Action.
U.S. Appl. No. 11/199,338, dated Jan. 25, 2007, Office Action.
U.S. Appl. No. 11/199,338, dated Oct. 5, 2007, Office Action.
U.S. Appl. No. 11/199,338, dated Dec. 28, 2007, Office Action.
U.S. Appl. No. 11/199,338, dated Apr. 23, 2008, Office Action.
U.S. Appl. No. 11/199,338, dated Jan. 6, 2009, Office Action.
U.S. Appl. No. 11/199,496, dated Apr. 1, 2009, Office Action.
U.S. Appl. No. 11/199,496, dated Aug. 21, 2009, Office Action.
U.S. Appl. No. 11/199,496, dated Apr. 23, 2010, Office Action.
U.S. Appl. No. 11/199,496, dated Apr. 28, 2011, Office Action.
U.S. Appl. No. 11/199,496, dated Aug. 18, 2011, Notice of Allowance.
U.S. Appl. No. 11/199,515, dated Aug. 20, 2008, Office Action.
U.S. Appl. No. 11/199,515, dated Nov. 13, 2008, Office Action.
U.S. Appl. No. 11/199,515, dated Jun. 10, 2009, Office Action.
U.S. Appl. No. 11/199,515, dated Dec. 24, 2009, Notice of Allowance.
U.S. Appl. No. 11/199,515, dated Apr. 2, 2010, Notice of Allowance.
U.S. Appl. No. 11/199,515, dated Aug. 2, 2010, Notice of Allowance.
U.S. Appl. No. 11/273,107, dated Jun. 14, 2007, Office Action.
U.S. Appl. No. 11/273,107, dated Jan. 18, 2008, Office Action.
U.S. Appl. No. 11/273,107, dated Sep. 5, 2008, Office Action.
U.S. Appl. No. 11/273,107, dated Apr. 9, 2009, Office Action.
U.S. Appl. No. 11/273,107, dated Oct. 28, 2009, Office Action.
U.S. Appl. No. 11/273,107, dated Jun. 2, 2010, Office Action.
U.S. Appl. No. 11/273,107, dated Oct. 27, 2010, Office Action.
U.S. Appl. No. 11/273,107, dated Jun. 2, 2011, Notice of Allowance.
U.S. Appl. No. 11/363,005, dated Jun. 22, 2007, Office Action.
U.S. Appl. No. 11/363,005, dated Dec. 14, 2007, Office Action.
U.S. Appl. No. 11/363,005, dated Apr. 17, 2008, Office Action.
U.S. Appl. No. 11/363,005, dated Dec. 23, 2008, Office Action.
U.S. Appl. No. 11/363,005, dated Jul. 10, 2009, Notice of Allowance.
U.S. Appl. No. 11/363,005, dated Jan. 14, 2010, Notice of Allowance.
U.S. Appl. No. 11/363,005, dated Jul. 23, 2010, Notice of Allowance.
U.S. Appl. No. 11/389,762, dated Sep. 20, 2007, Notice of Allowance.

(56) References Cited

OTHER PUBLICATIONS

U.S. Appl. No. 11/389,762, dated Nov. 23, 2007, Notice of Allowance.
U.S. Appl. No. 11/390,937, dated Sep. 7, 2007, Office Action.
U.S. Appl. No. 11/391,951, dated Oct. 28, 2008, Office Action.
U.S. Appl. No. 11/391,951, dated Jan. 30, 2009, Office Action.
U.S. Appl. No. 11/391,951, dated Aug. 26, 2009, Office Action.
U.S. Appl. No. 11/391,951, dated Jun. 23, 2010, Office Action.
U.S. Appl. No. 11/465,527, dated Feb. 3, 2010, Office Action.
U.S. Appl. No. 11/465,527, dated Jul. 23, 2010, Notice of Allowance.
U.S. Appl. No. 11/552,593, dated Aug. 21, 2008, Office Action.
U.S. Appl. No. 11/552,593, dated Feb. 5, 2009, Office Action.
U.S. Appl. No. 11/552,593, dated Oct. 13, 2009, Notice of Allowance.
U.S. Appl. No. 11/552,593, dated Mar. 22, 2010, Notice of Allowance.
U.S. Appl. No. 11/552,593, dated Jul. 22, 2010, Notice of Allowance.
U.S. Appl. No. 11/688,722, dated Mar. 10, 2010, Office Action.
U.S. Appl. No. 11/688,722, dated Jul. 29, 2010, Notice of Allowance.
U.S. Appl. No. 11/891,358, dated Apr. 26, 2010, Office Action.
U.S. Appl. No. 11/891,358, dated Oct. 19, 2010, Office Action.
U.S. Appl. No. 11/891,358, dated Aug. 31, 2011, Office Action.
U.S. Appl. No. 11/891,358, dated Nov. 18, 2011, Notice of Allowance.
U.S. Appl. No. 11/891,358, dated Apr. 10, 2012, Notice of Allowance.
U.S. Appl. No. 11/891,513, dated Apr. 9, 2010, Office Action.
U.S. Appl. No. 11/891,513, dated Sep. 28, 2010, Office Action.
U.S. Appl. No. 11/891,513, dated Aug. 31, 2011, Office Action.
U.S. Appl. No. 11/891,513, dated Nov. 1, 2011, Notice of Allowance.
U.S. Appl. No. 11/891,513, dated May 8, 2012, Notice of Allowance.
U.S. Appl. No. 11/960,593, dated Sep. 14, 2010, Office Action.
U.S. Appl. No. 11/960,593, dated Nov. 3, 2010, Office Action.
U.S. Appl. No. 11/960,593, dated Apr. 28, 2011, Office Action.
U.S. Appl. No. 11/960,593, dated Jul. 1, 2013, Notice of Allowance.
U.S. Appl. No. 11/997,379, dated Jul. 13, 2011, Office Action.
U.S. Appl. No. 11/997,379, dated Feb. 28, 2012, Office Action.
U.S. Appl. No. 11/997,379, dated May 11, 2012, Notice of Allowance.
U.S. Appl. No. 12/182,836, dated Oct. 5, 2010, Office Action.
U.S. Appl. No. 12/182,836, dated Jun. 23, 2011, Office Action.
U.S. Appl. No. 12/182,836, dated May 17, 2013, Office Action.
U.S. Appl. No. 12/247,012, dated Oct. 13, 2011, Office Action.
U.S. Appl. No. 12/247,012, dated Mar. 16, 2012, Office Action.
U.S. Appl. No. 12/247,012, dated Aug. 13, 2012, Notice of Allowance.
U.S. Appl. No. 12/257,127, dated Aug. 30, 2010, Office Action.
U.S. Appl. No. 12/257,127, dated Dec. 22, 2010, Office Action.
U.S. Appl. No. 12/257,127, dated Jul. 6, 2011, Office Action.
U.S. Appl. No. 12/257,127, dated Jan. 12, 2012, Office Action.
U.S. Appl. No. 12/257,127, dated Sep. 20, 2012, Notice of Allowance.
U.S. Appl. No. 12/334,077, dated Oct. 27, 2010, Office Action.
U.S. Appl. No. 12/334,077, dated Jul. 21, 2011, Office Action.
U.S. Appl. No. 12/334,077, dated Jan. 16, 2013, Office Action.
U.S. Appl. No. 12/334,077, dated Oct. 11, 2013, Notice of Allowance.
U.S. Appl. No. 12/334,085, dated Dec. 23, 2010, Office Action.
U.S. Appl. No. 12/334,085, dated Aug. 4, 2011, Office Action.
U.S. Appl. No. 12/334,085, dated Jan. 9, 2012, Notice of Allowance.
U.S. Appl. No. 12/873,728, dated Sep. 11, 2012, Office Action.
U.S. Appl. No. 12/873,728, dated May 3, 2013, Office Action.
U.S. Appl. No. 12/873,728, dated Aug. 23, 2013, Office Action.
U.S. Appl. No. 12/873,728, dated Nov. 4, 2013, Notice of Allowance.
U.S. Appl. No. 12/950,338, dated Jun. 15, 2011, Office Action.
U.S. Appl. No. 12/950,338, dated Nov. 1, 2011, Notice of Allowance.
U.S. Appl. No. 12/950,338, dated Aug. 8, 2012, Notice of Allowance.
U.S. Appl. No. 12/955,848, dated Jun. 30, 2011, Office Action.
U.S. Appl. No. 12/955,848, dated Nov. 15, 2011, Office Action.
U.S. Appl. No. 12/955,863, dated Jan. 6, 2012, Office Action.
U.S. Appl. No. 12/955,863, dated May 15, 2012, Notice of Allowance.
U.S. Appl. No. 12/955,869, dated Oct. 18, 2011, Office Action.
U.S. Appl. No. 12/955,869, dated Mar. 22, 2012, Notice of Allowance.
U.S. Appl. No. 12/961,239, dated Jul. 26, 2011, Notice of Allowance.
U.S. Appl. No. 12/966,961, dated Aug. 18, 2011, Notice of Allowance.
U.S. Appl. No. 13/022,050, dated Jul. 11, 2011, Office Action.
U.S. Appl. No. 13/022,050, dated Apr. 26, 2012, Office Action.
U.S. Appl. No. 13/022,050, dated Jul. 6, 2012, Notice of Allowance.
U.S. Appl. No. 13/333,411, dated Dec. 18, 2014, Office Action.
U.S. Appl. No. 13/333,411, dated Apr. 1, 2015, Office Action.
U.S. Appl. No. 13/443,659, dated Nov. 13, 2013, Office Action.
U.S. Appl. No. 13/443,659, dated Jun. 11, 2014, Notice of Allowance.
U.S. Appl. No. 13/455,053, dated Nov. 27, 2013, Office Action.
U.S. Appl. No. 13/455,053, dated Jun. 9, 2014, Notice of Allowance.
U.S. Appl. No. 13/485,388, dated May 21, 2015, Office Action.
U.S. Appl. No. 13/525,875, dated May 28, 2014, Office Action.
U.S. Appl. No. 13/525,875, dated Sep. 30, 2014, Office Action.
U.S. Appl. No. 13/525,875, dated Dec. 10, 2014, Notice of Allowance.
U.S. Appl. No. 13/593,154, dated Jan. 8, 2013, Notice of Allowance.
U.S. Appl. No. 13/615,530, dated Jan. 17, 2013, Office Action.
U.S. Appl. No. 13/615,530, dated Jun. 12, 2013, Notice of Allowance.
U.S. Appl. No. 13/752,095, dated Oct. 17, 2014, Office Action.
U.S. Appl. No. 13/752,095, dated Feb. 20, 2015, Office Action.
U.S. Appl. No. 13/752,095, dated Jun. 12, 2015, Notice of Allowance.
U.S. Appl. No. 13/870,628, dated Jul. 13, 2015, Office Action.
U.S. Appl. No. 14/094,352, dated Dec. 15, 2014, Office Action.
U.S. Appl. No. 14/094,352, dated Jul. 8, 2015, Office Action.
U.S. Appl. No. 14/195,308, dated Dec. 18, 2014, Office Action.
U.S. Appl. No. 90/006,469, dated Nov. 29, 2002, Request for Re-Examination.
U.S. Appl. No. 90/006,469, dated Sep. 10, 2004, Office Action.
U.S. Appl. No. 90/006,469, dated Sep. 27, 2005, Notice of Re-Issue.
U.S. Appl. No. 90/006,469, dated Jun. 27, 2006, Re-Examination Certification.

* cited by examiner

SYSTEMS FOR ANCHORING A MEDICAL DEVICE IN A BODY LUMEN

CROSS-REFERENCE TO RELATED APPLICATIONS

This application is a continuation of U.S. patent application Ser. No. 13/525,875, filed Jun. 18, 2012, now U.S. Pat. No. 8,998,932, which is a continuation of U.S. patent application Ser. No. 12/955,869, filed Nov. 29, 2010, now U.S. Pat. No. 8,202,281, which is a continuation of Ser. No. 11/552,593, filed Oct. 25, 2006, now U.S. Pat. No. 7,842,049, which is a divisional application of U.S. patent application Ser. No. 10/335,147, filed Dec. 31, 2002, now U.S. Pat. No. 7,160,309, the entire contents of which are incorporated by reference herein.

BACKGROUND OF THE INVENTION

1. The Field of the Invention

The present invention relates in general to systems for anchoring medical devices in body lumens, or body cavities. In particular, the present invention relates to systems for anchoring catheters in body lumens, which may include blood vessels.

2. The Relevant Technology

Various medical procedures require the anchoring of a medical device within a body lumen. All of these systems need to be designed so that the device can be removed at the end of the procedure without causing unacceptable amounts tissue damage. For example, in the case of a catheter anchored in a blood vessel, the catheter must be easily inserted through an opening in the side of the vessel yet also be easily anchored when positioned at its desired location in the vessel.

A variety of systems have been designed to anchor a catheter passing into a body lumen through an opening in the side of the body lumen. Most commonly, an inflatable balloon is mounted on the catheter. After the catheter has been positioned at a desired location, the balloon is inflated. The balloon thereby pushes against the walls of the body lumen adjacent to the side opening when the catheter is pulled back, thus holding the catheter in position. Unfortunately, a problem with using such an inflatable balloon is that it typically blocks fluid flow through the lumen, which may not be desirable. Also, in addition to inhibiting fluid circulation, the balloon may interfere with drug delivery systems in the catheter.

What is instead desired is a simple system for securing a medical device such as a catheter in a body lumen. Such a system would preferably not interfere with fluid flow through the body lumen (such as blocking fluid flow with an inflatable balloon). In addition, such an anchoring system would preferably be easily removable at the end of the medical procedure.

BRIEF SUMMARY OF THE INVENTION

The present invention provides a versatile system for securing a medical device (such as a catheter) at preferred locations within a body lumen (such as a blood vessel) without blocking or substantially inhibiting fluid flow through the lumen.

In preferred embodiments, the present invention includes a sheath having a plurality of side openings; a rotatable element disposed within the sheath; and a plurality of curved projections extending from the rotatable element, wherein rotation of the rotatable element with respect to the sheath pushes distal ends of each of the curved projections outwardly through one of the plurality of openings. In preferred methods of use, the plurality of curved projections are extended outwardly from the rotatable element and are then used to brace against the tissue surrounding a side hole opening into the vessel. Thus, when the device is deployed within the body lumen, and then pulled back (ie: proximally), the curved projections contact the tissue surrounding the side opening into the vessel, thereby preventing the device from being removed. The deployed projections may also provide needle receiving locations in the case of a suturing device, such as a device for suturing an arteriotomy.

The present invention also includes an embodiment including a sheath having only one side opening with one curved projection extending from the rotatable element. Similar to the above design, rotation of the rotatable element with respect to the sheath pushes the distal end of the curved projection outwardly through the side opening. In this embodiment, the curved projection may be a wire having one end attached to the rotatable element.

In optional preferred embodiments, the curved projection(s) may be biased to spring radially outwardly as they pass through the side opening(s) in the sheath. Alternatively, or in addition, the curved projection(s) may be formed from a shape memory material which assists them in springing radially outwards as they pass through the side opening(s) in the sheath.

In various embodiments, the curved projection(s) may either be attached to the rotatable element, or they may be integrally formed into the rotatable element.

In various preferred embodiments, the curved projections are opposite ends of a deformable element such as a wire or ribbon. Most preferably, such deformable element passes through (or is fitted around) the central rotatable element.

The present invention also provides a method of anchoring a device in a body lumen or cavity, including inserting the device into the body lumen or cavity, and rotating the rotatable element with respect to the sheath, thereby causing the distal ends of each of the curved projections to move outwardly through one of the one or more openings and into the body lumen or cavity. In preferred embodiments of the present method, the body lumen may be any blood vessel.

DETAILED DESCRIPTION OF THE PREFERRED EMBODIMENTS

FIGS. 1A to 3B illustrate a first embodiment of the invention which deploys two curved projections that can be used as an anchor against tissue surrounding an opening into a vessel lumen. In this particular example, the two curved projections are opposite ends of a single ribbon shaped element which passes through a central rotatable element of the device. The present invention is not so limited. Rather, other embodiments are also contemplated.

Figure 5A:
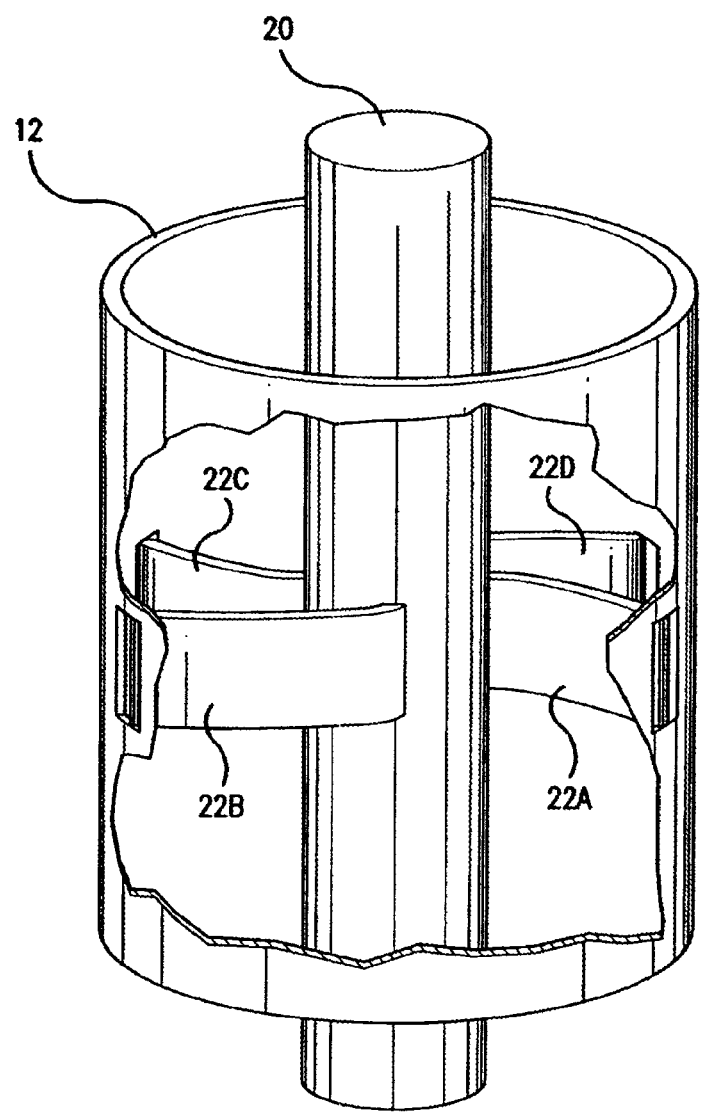
FIG. 5A is a perspective view of a third embodiment of the invention prior to its deployment.
Figure 5B:
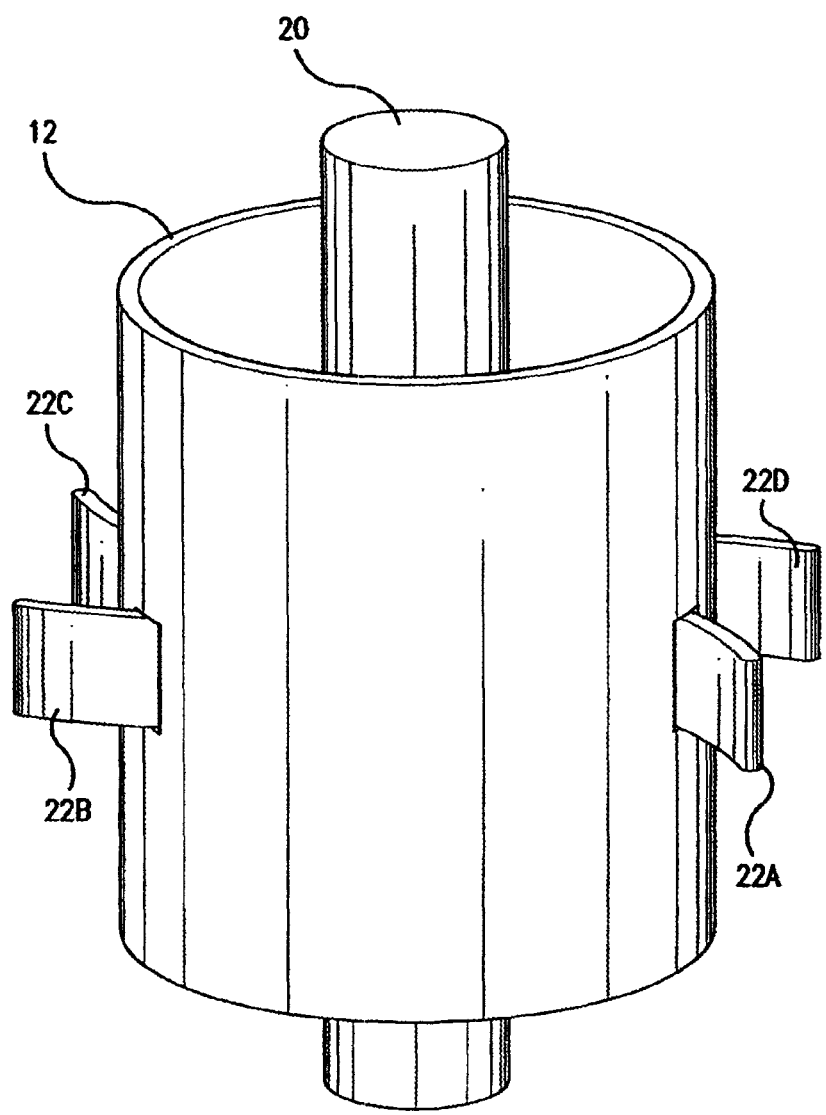
FIG. 5B is a perspective view of the third embodiment of the invention after it has been deployed.
Figure 6A:
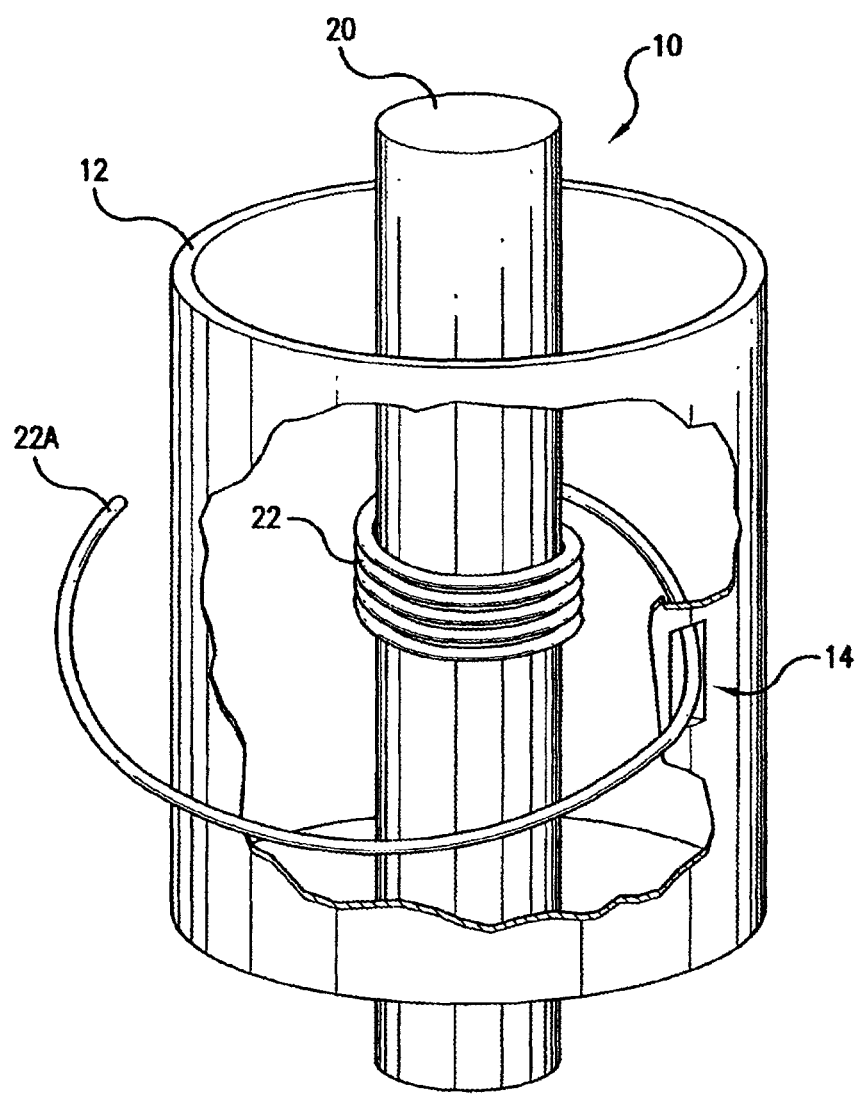
FIG. 6A is a perspective view of a fourth embodiment of the invention having only one side opening in the sheath.
Figure 6B:
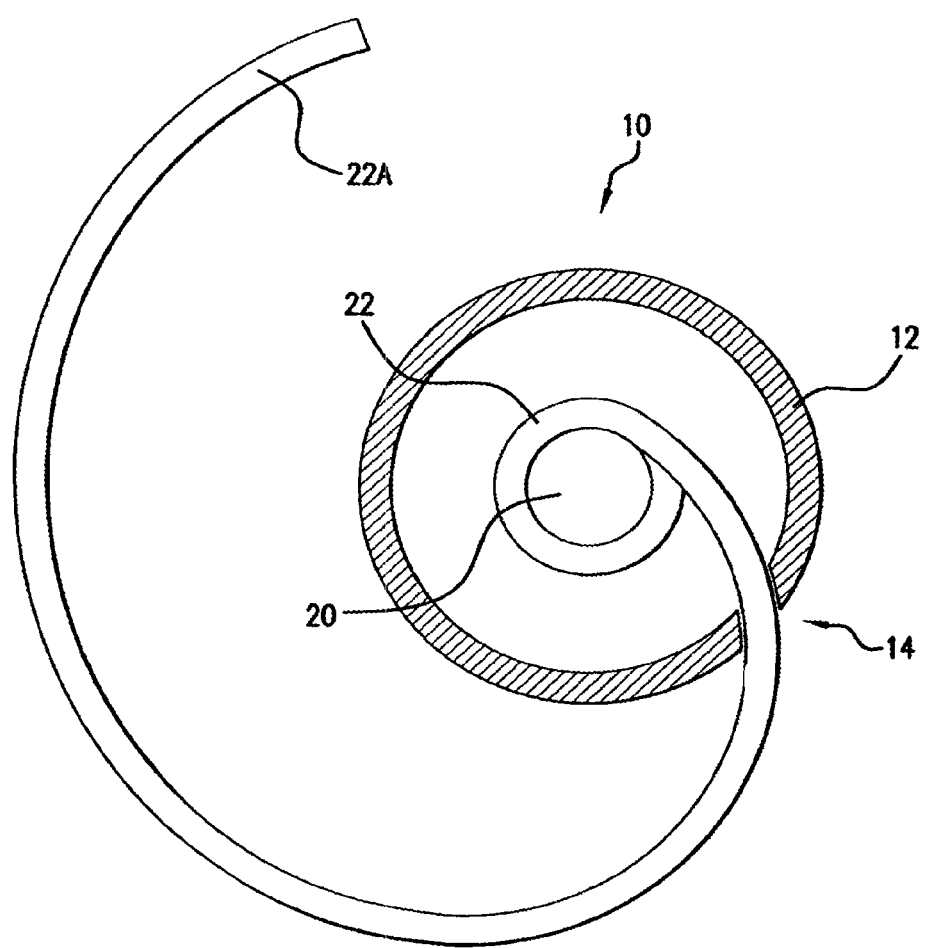
FIG. 6B is a sectional elevation view corresponding to FIG. 6A.
Figure 7A:
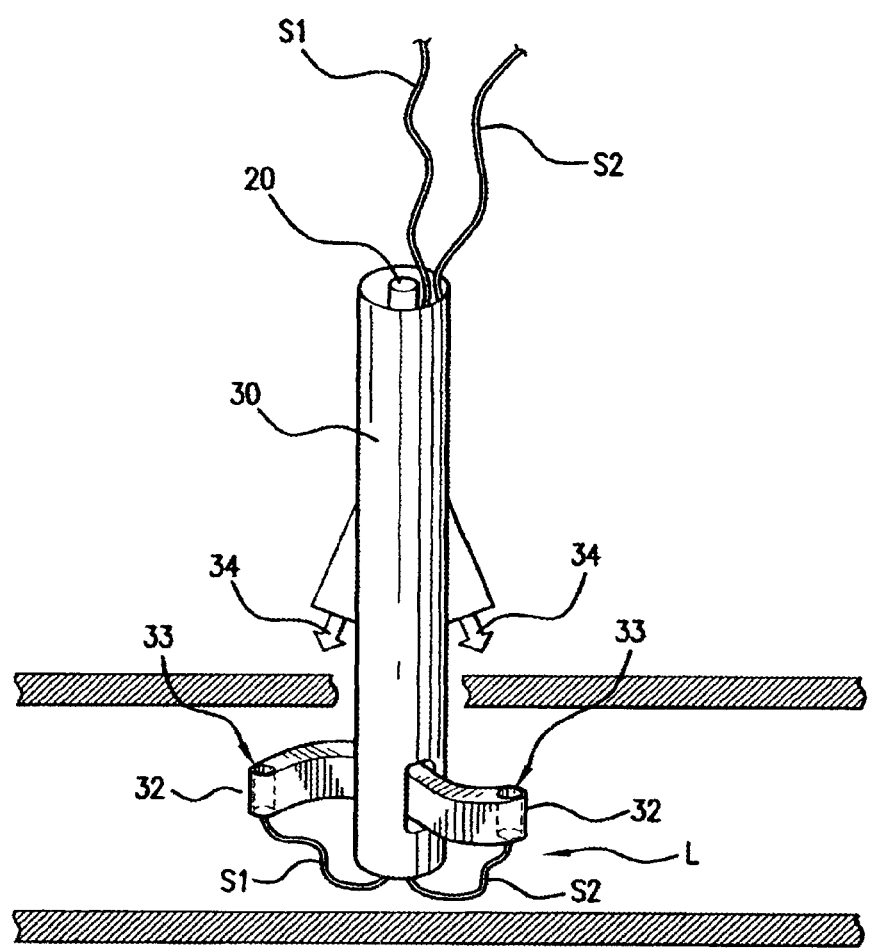
FIG. 7A is a perspective view of a fifth embodiment of the invention, in which the invention comprises a suturing device, after its arms have been deployed, but prior to suturing a tissue hole.
Figure 7B:
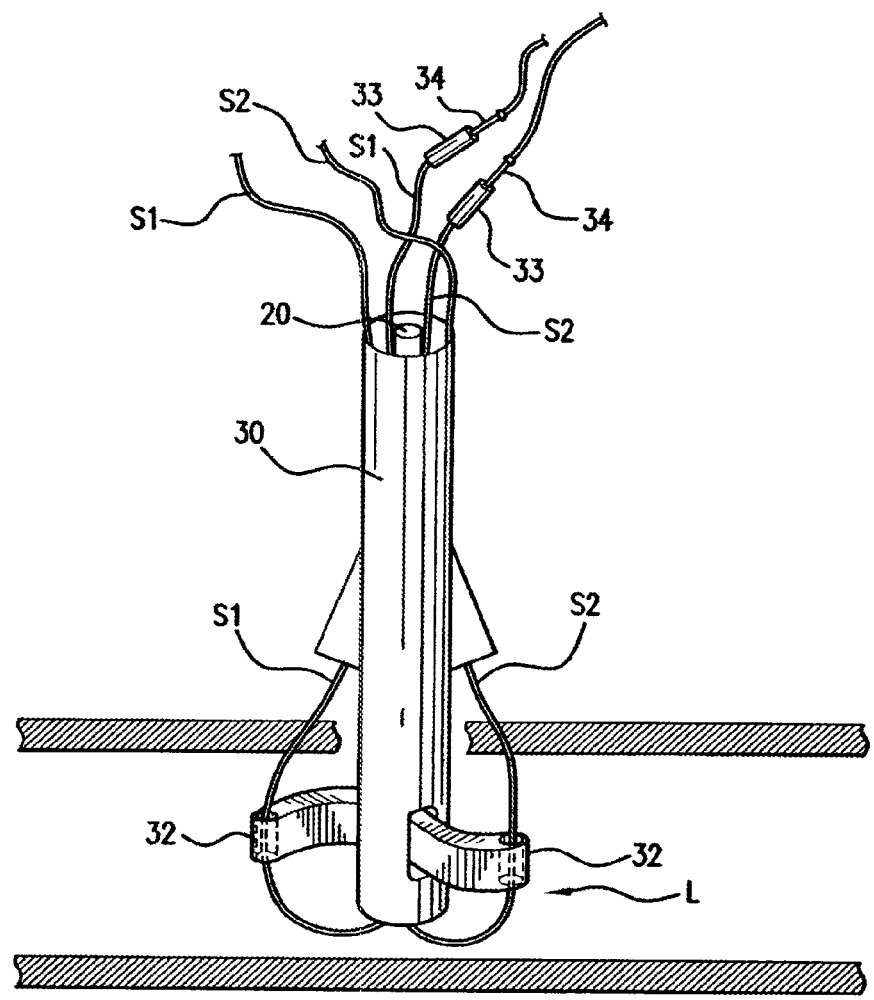
FIG. 7B is a perspective view corresponding to FIG. 7A, but after the tissue hole has been sutured.

For example, FIGS. 4A and 4B illustrate a second embodiment of the invention which deploys four curved projections. This embodiment is similar to the first embodiment, but instead uses two ribbon shaped elements which are spaced longitudinally apart from one another. FIGS. 5A and 5B illustrate a third embodiment of the invention which deploys four curved projections into the tissue. In this particular example, the curved projections may either be attached to the central rotatable element, or may be integrally formed with the central rotatable element. FIGS. 6A and 6B illustrate a fourth embodiment of the invention which deploys a single curved projection in the form of a wire attached at one end to the central rotatable element. Lastly, FIGS. 7A and 7B illustrate a fifth embodiment of the invention in which a suturing device includes needles and suture in operative relationships with the anchoring elements or projections.

Each of the four embodiments of the invention (FIGS. 1A to 6B) illustrate the present invention as incorporated into a catheter system. Thus, for clarity, each of FIGS. 1A, 1B, and 4 to 6B illustrates only a cut-out longitudinal section of a catheter system in which the present invention is incorporated. FIGS. 3A and 3B show a greater length of the catheter. As can be appreciated, the catheter extends upwardly and/or downwardly perpendicular from the page in FIGS. 2A and 2B.

Figure 1A:
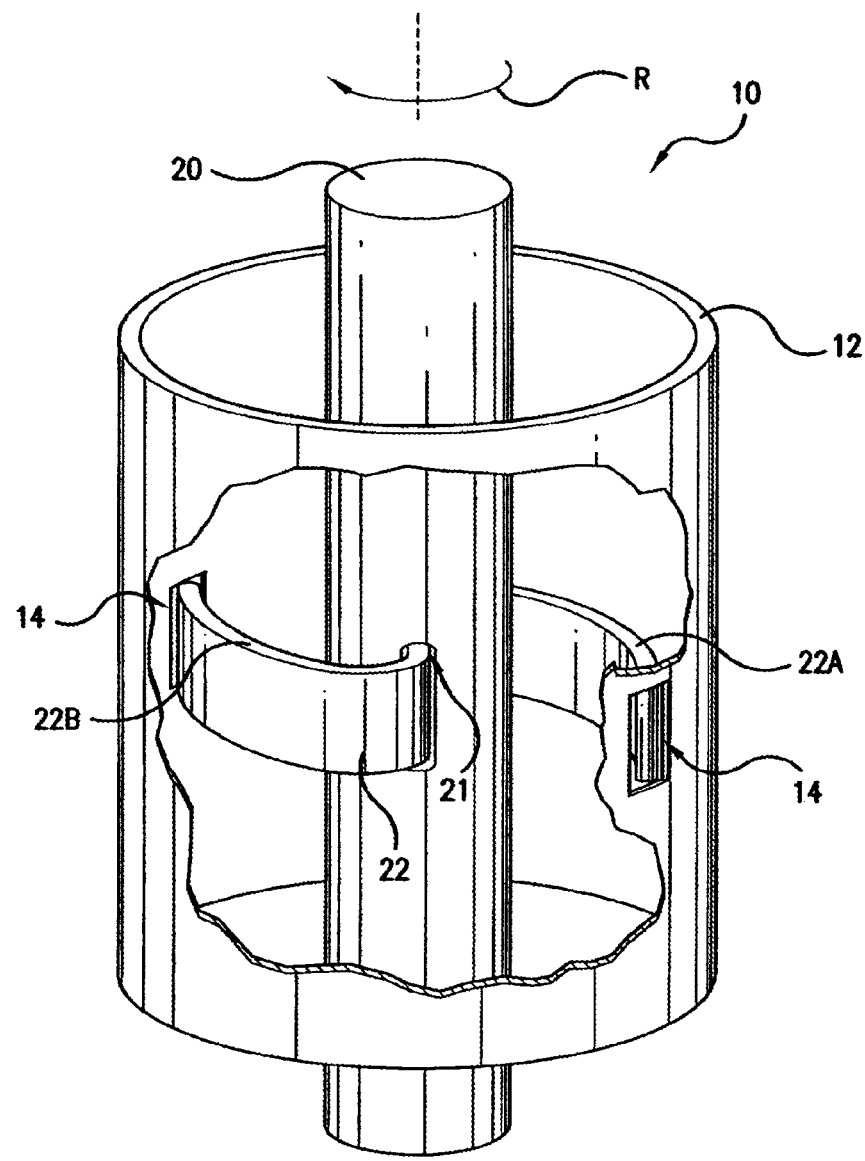
FIG. 1A is a perspective view of a first embodiment of the invention prior to its deployment.
Figure 2A:
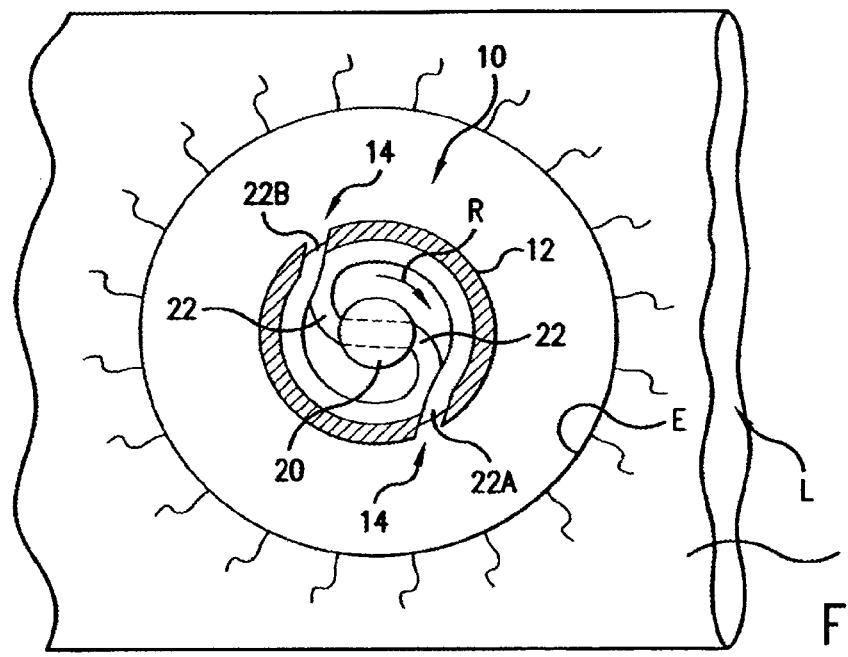
FIG. 2A is a top plan view corresponding to FIG. 1A, showing the device passing through a side opening in a vessel lumen, with the distal end of the device positioned within the vessel lumen.
Figure 3A:
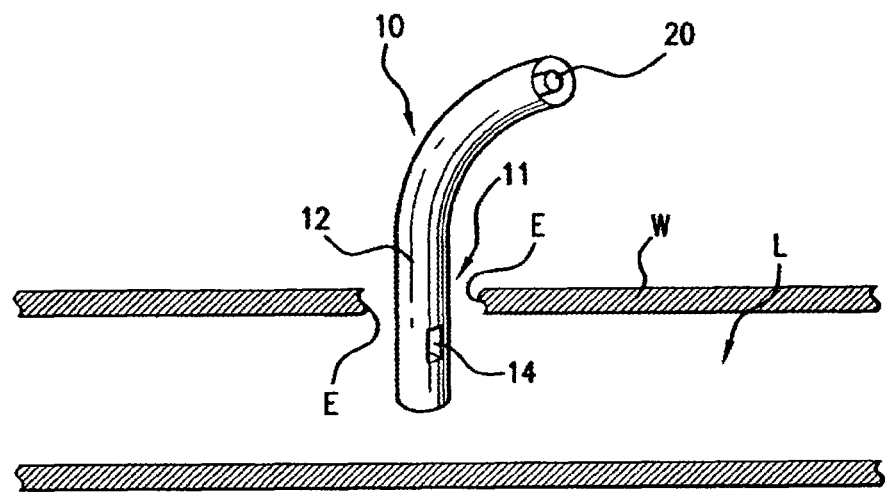
FIG. 3A is a side view corresponding to FIG. 2A.
Figure 3B:
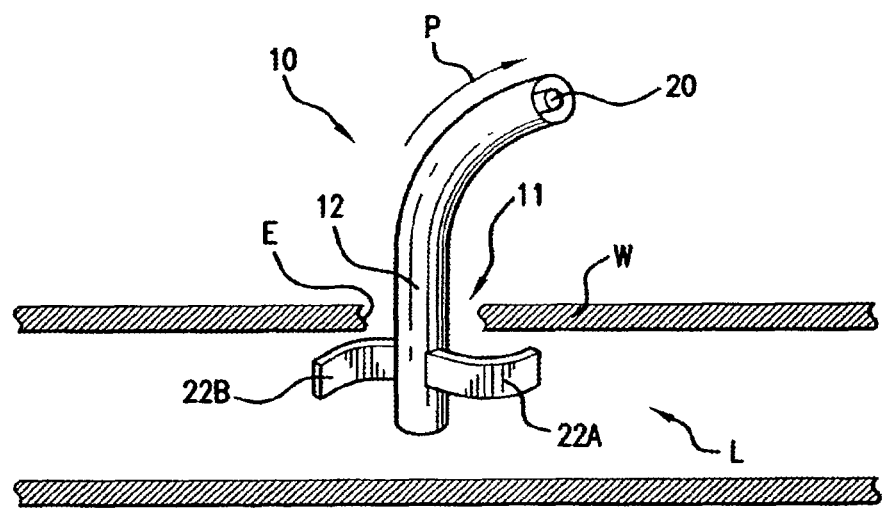
FIG. 3B is a side view corresponding to FIG. 2B.

Referring first to FIGS. 1A, 2A and 3A, a system 10 for securing a catheter system in a body lumen is provided. Sheath 12 has a pair of side openings 14 disposed on opposite sides thereof. A central rotatable element 20 is received within sheath 12. A pair of projections 22A and 22B extend radially outwardly from rotatable element 20, as shown in FIGS. 1A, 2A and 3A. The sheath described herein may be a portion of a catheter body, an introducer sheath, or simply a hollow tubular body that is part of a device into which the present invention is incorporated. As will also be explained and illustrated, the present invention may be used in applications other than in a catheter body. For example, the present invention may be incorporated into a suturing device as shown in FIGS. 7A and 7B. It is to be understood, however, that the present invention may be incorporated into other devices as well.

Figure 1B:
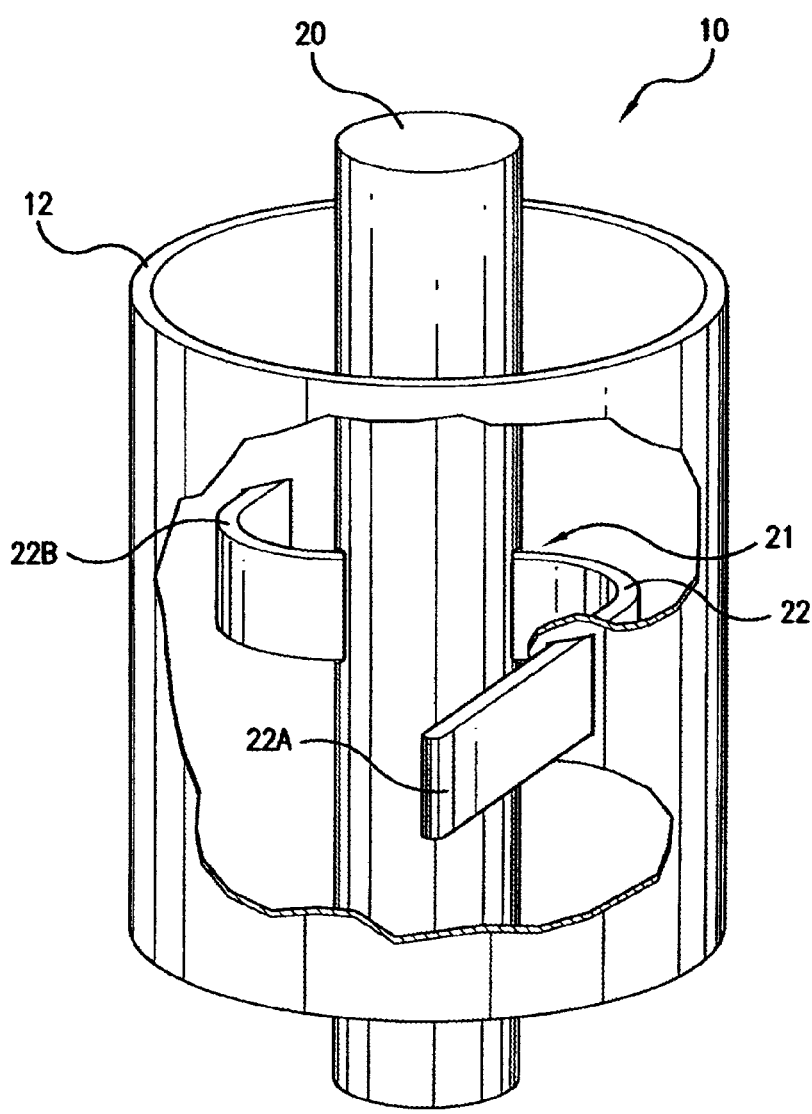
FIG. 1B is a perspective view of the first embodiment of the invention after it has been deployed.
Figure 2B:
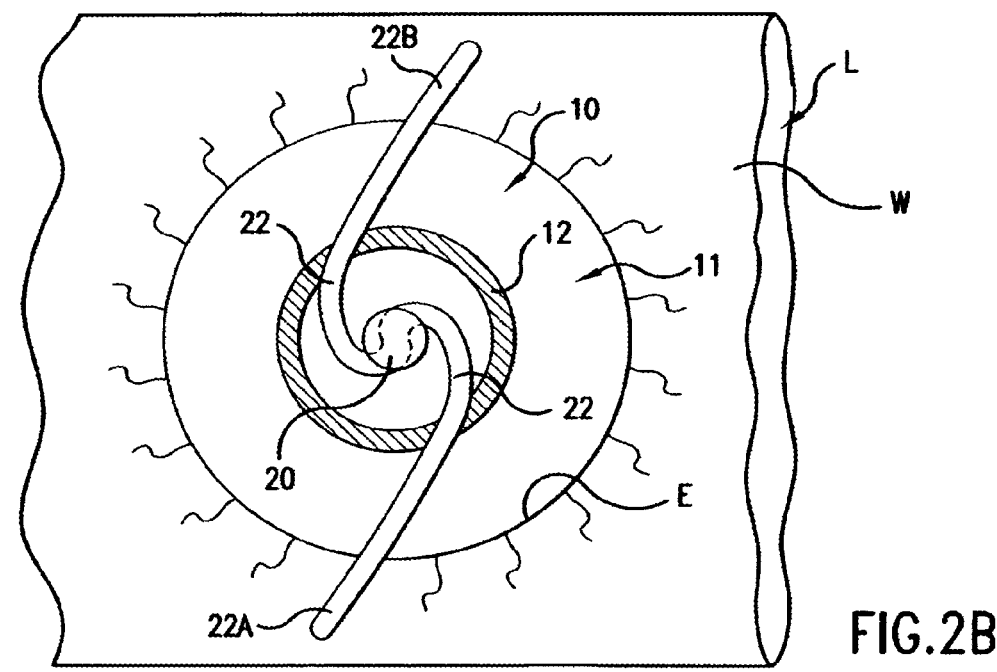
FIG. 2B is a top plan view corresponding to FIG. 1B, showing the device passing through a side opening in a vessel lumen, with the distal end of the device anchored in the vessel lumen.

Returning to FIGS. 1A, 2A and 3A, rotation of rotatable element 20 within sheath 12 in direction R (FIG. 2A) causes the distal ends of each of projections 22A and 22B to be pushed out through openings 14. Thus, rotation of rotatable element 20 with respect to sheath 12 in direction R moves curved projections 22A and 22B from the pre-deployed position (FIGS. 1A, 2A and 3A) to the fully deployed position (FIGS. 1B, 2B and 3B). As can be seen in FIG. 3B, such deployment causes curved projections 22A and 22B to extend beyond the edges E of side hole 11 in the wall W of body lumen L. Thus, curved projections 22A and 22B can act as an anchoring system, such that they will push against the interior surface of wall W when the catheter system 10 is pulled proximally in direction P.

It is to be understood that all reference herein made to rotation of the rotatable element (which is disposed within the sheath) both in the specification and claims, refers to rotation of the rotatable element with respect to the sheath. Thus, "rotation of the rotatable element" in the specification and claims, encompasses rotation of the rotatable element with the sheath held stationary, rotation of the sheath with the rotatable element held stationary, rotation of the sheath and rotatable element in opposite directions, and rotation of the sheath and rotatable element in the same direction, but at different speeds.

As can be appreciated, removal of the present anchoring system is accomplished by simply rotating rotatable element 20 with respect to sheath 12 in a direction opposite to R, thereby retracting curved projections 22A and 22B into the sheath.

As shown in FIGS. 1A to 3B, curved projections 22A and 22B move through side openings 14 which are disposed on opposite sides of sheath 12. Thus, in various embodiments, any number of side openings 14 may be disposed equidistantly around the circumference of sheath 12.

Projections 22A and 22B may be curved. The projections preferably extend radially from the rotatable element in a plane that may be perpendicular or otherwise transverse to the longitudinal axis of the device or to the rotatable element. Specifically, the projections 22A and 22B move through side openings 14 as the projections are deployed in a radial direction with respect to the axis of the device. Such movement in the radial direction may preferably be confined to movement in the transverse plane defined by the lengths of the projections.

In the preferred embodiment illustrated in FIGS. 1A to 3B, projections 22A and 22B are simply opposite ends of a single deformable member 22 which passes through a hole 21 in rotatable element 20. Deformable member 22 (and its curved projections 22A and 22B) may be formed from a ribbon shaped material (having a rectangular cross section, as shown). Alternatively, deformable member 22 (and its curved projections 22A and 22B) may be formed from a wire (having a circular cross section). In further embodiments, deformable member 22 (and its curved projections 22A and 22B) may be formed from a member having an I-beam cross section.

An advantage of curved projections 22A and 22B being ribbon shaped or I beam shaped (or any other dimension in which they are thicker in the direction along the length of sheath 12) is that they are more resistant to bending when the catheter is pulled in direction P, such that the projections push against the tissue surrounding the interior of opening 11 through tissue wall W (see FIG. 3B).

It is to be understood that although curved projections 22A and 22B may be opposite ends of a single deformable member 22 (as shown), curved projections 22A and 22B may also be two separate elements which either are fastened to rotatable element 20 or are integrally formed from the same block of material as rotatable element 20. Whether or not curved projections 22A and 22B are opposite ends of a single member, or are separate elements, such curved projections are preferably formed from a deformable material. Suitable deformable materials may include (but are not limited to) metals, including shape memory metals, polymers, or any combinations thereof In optional preferred embodiments, curved projections 22A and 22B may be formed of a material which causes them to be biased such that their ends spring radially outwardly (i.e.: straighten out) as they pass through side openings 14. An example of this effect can be seen in FIG. 2B where the curved radially extending ends of projections 22A and 22B are shown as being straighter than the center portion of deformable member 22 that is inside sheath 12. This is advantageous in that it is the straightest portion of deformable member 22 protrudes radially away from the center of the device, and reaching farther, thus maximizing the amount of tissue against which the projections are anchored.

Optionally, curved projections 22A and 22B may be formed of a shape memory material (such as Nitinol). As such, curved projections 22A and 22B may thus be formed to spring radially outwardly (i.e.: straighten out) when they are exposed to a temperature change. For example, curved projections 22A and 22B could be exposed to a temperature change as they exit windows 14 by being warmed by the fluid passing through the body lumen.

Figure 4:
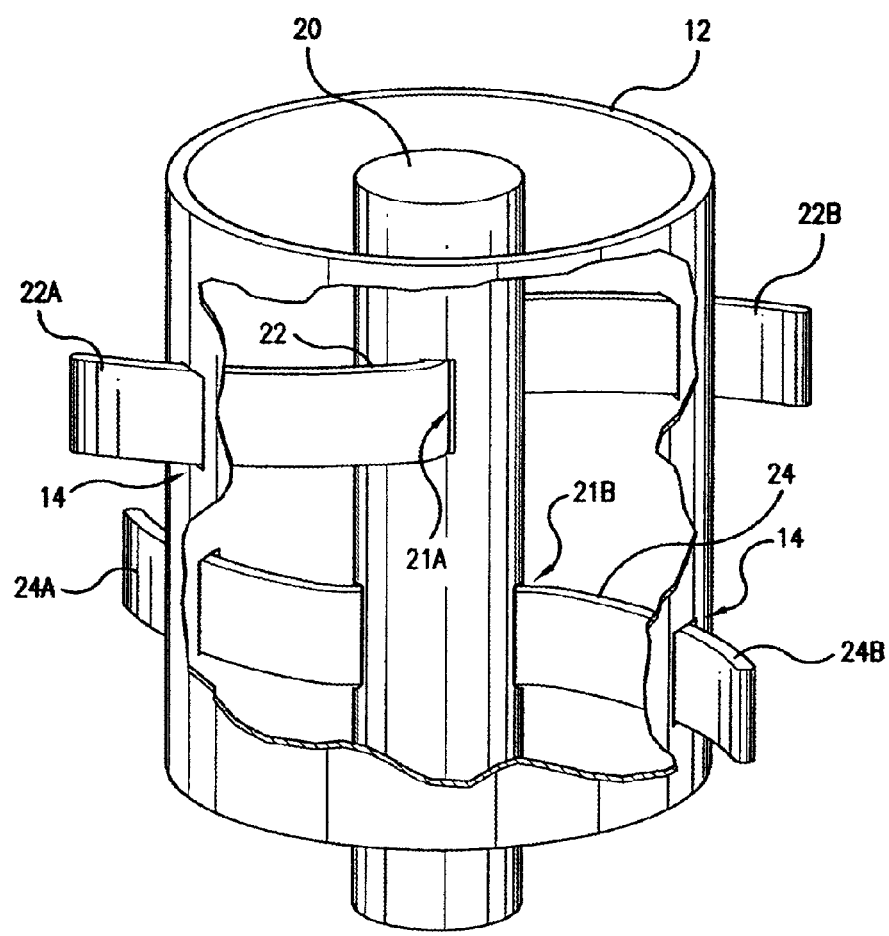
FIG. 4 is a perspective view of a second embodiment of the invention.

FIG. 4 illustrates an embodiment of the invention having two pairs of curved projections. Specifically, a first pair comprising curved projections 22A and 22B, and a second pair comprising curved projections 24A and 24B. Thus, in this embodiment side openings 14 are also disposed longitudinally along the length of the sheath (as well as about the circumference of the shaft). As illustrated, curved projections 22A and 22B are opposite ends of a first deformable element 22 passing through hole 21A while 24A and 24B are opposite ends of a second deformable element 24 passing through hole 21B.

FIGS. 5A and 5B illustrate yet another embodiment of the invention in which four curved projections 22A, 22B, 22C and 22D each extend from central rotatable element 20. In this embodiment, four curved projections are used. It is to be understood however that, in accordance with the present invention, any plurality of curved projections can be used. These curved projections protrude through openings which may be disposed equidistantly around the circumference of shaft 12. For example, curved projections 22A, 22B, 22C and 22D are shown as disposed at 90 degrees to one another.

FIGS. 6A and 6B illustrate yet another embodiment of the invention in which a single curved projection 22A is deployed through a single side opening 14. In this embodiment, curved projection 22A is one end of a wire (or other suitable deformable member) 22 which is wrapped around (and attached at one end to) central rotatable element 20. In this embodiment, the length of wire 22 may optionally be as long, or longer than, deformable member 22 as shown in the other embodiments. Thus, wire 22 can be rotated such that its distal end (curved projection 22A) is deployed much father through side opening 14 than is shown in the previous embodiments. This would have the effect of causing wire 22, and its distal end (i.e. curved projection 22A) to extend farther around the circumference of sheath 12, thus firmly anchoring the present device in position. FIGS. 6A and 6B show wire 22 extending approximately half way around the circumference of the device. It is to be understood that the distal end of wire 22 (i.e. curved projection 22A) may also—extend even further around the circumference of the device. For example, the distal end of wire 22 may be extended fully around the device, or even further (so that it wraps around the circumference of the device several times).

In various embodiments, the present invention is substantially enclosed within the body of the catheter, thus saving space and permitting easy access into the interior of body lumen L.

In various preferred embodiments, the present system is dimensioned to be around 5 to 10 mm in diameter, but may instead be dimensioned smaller so that it may fit into vessels less than 5 mm in diameter.

The various embodiments of the invention which are incorporated into a catheter system do not block fluid flow when anchoring a catheter in a body lumen. Thus, the present invention may conveniently be used in conjunction with systems either for drug or therapeutic energy delivery, or with diagnostic systems.

In an alternate embodiment, shown in FIGS. 7A and 7B, the device is a suturing device 30 that is anchored on the interior side of a vessel wall through an arteriotomy. The device 30 may include suture-carrying or holding features located on extendable projections 32 in order to retrieve sutures S1 and S2 when device 30 provides an arteriotomy closure. In accordance with this embodiment, projections 32 are deployed radially outwardly in the same fashion that projections 22 were deployed in the previously described embodiments (eg: by rotating rotatable element 20 within device 30).

The suture-carrying features may be recesses formed in projections 32. For example, the suture-carrying features may include cuffs 33 that may be attached to the ends SI and S2 of a length of suture which runs through the center of device 30. Cuffs 33 can be held within recesses in projections 32. The present suture-carrying features may include cuffs, but the present invention is not so limited. For example, the ends of the suture can alternatively be formed into other features that are connectable to needles, such as loops. Suturing device 30 further comprises a pair of needles 34 that are initially disposed on an exterior of lumen L as shown in FIG. 7A. Thereafter, needles 34 are advanced so that they pass through the wall of the vessel, such that each needle 34 is received into a cuff 33. Thereafter, needles 34 are retracted, as shown in FIG. 7B, each pulling a cuff 33 with a length of suture (Si or S2) attached thereto out of the proximal end of device 30. Thereafter, extendable projections 32 can be retracted radially inwardly (by rotating element 20 in an opposite direction) so that the distal end of device 30 may be removed from the hole in the side of the artery, leaving behind suture passing therethrough, which can be used to close the hole. It is to be understood that although device 30 is illustrated as having two needles 34, cuffs 33 and sutures Si and S2, other embodiments having more needles, cuffs and sutures are also possible. As illustrated in FIGS. 7A and 7B, the needles of such a device are would engage the cuffs and pull the suture through tissue.

What is claimed is:

1. A system comprising:
    an elongate member having an anchor member extending transversely from the elongate member, the anchor member having a rectangular cross-section, the rectangular cross-section having a larger dimension in a longitudinal direction of the elongate member to resist bending in the longitudinal direction; and
    a sheath having a lumen and a closed perimeter, sidewall opening communicating with the lumen, the sheath receiving the elongate member, the anchor member springs transversely outwardly through the sidewall opening with respect to a longitudinal axis of the sheath to a deployed configuration, wherein rotating the sheath selectively deploys or retracts the anchor member into the lumen of the sheath.

2. The system as recited in claim 1, wherein the anchor member is integrally formed with the elongate member.

3. The system as recited in claim 1, wherein the anchor member is fastened to the elongate member.

4. The system as recited in claim 1, wherein the sidewall opening has a larger dimension in a longitudinal dimension of the sheath.

5. The system as recited in claim 1, wherein the sidewall opening in the sheath has an angled portion extending from an inner surface to an outer surface of the sheath.

6. The system as recited in claim 1, wherein the sidewall opening has a proximal end proximal a distal end of the sheath.

7. The system as recited in claim 1, wherein the sidewall opening longitudinally extends towards a distal end of the sheath.

8. The system of claim 1, wherein the anchor member is positioned proximal a distal end of the elongate member.

9. A system for anchoring in tissue, comprising
a central element having a plurality of anchor members extending from the central element, the plurality of anchor members each having a rectangular cross-section, the rectangular cross-section having a dimension thicker in a direction along a length of the central element to resist bending in the longitudinal direction, and a generally cylindrical sheath configured to receive the central element and the plurality of anchor members, the sheath having a plurality of closed perimeter, sidewall openings disposed equidistant around a circumference of the sheath, the sheath having a proximal end, a distal end and a longitudinal axis extending therebetween, wherein, as the central element is rotated about the longitudinal axis of the sheath, at least one of the plurality of anchor members springs, transverse to the axis of the sheath, outwardly into the tissue through at least one of the sidewall openings to a deployed configuration.

10. The system as recited in claim 9, wherein each anchor member is integrally formed with or fastened to the central element.

11. The system as recited in claim 9, wherein each sidewall opening has a larger dimension in a longitudinal dimension of the sheath.

12. The system as recited in claim 9, wherein the sidewall opening longitudinally extends towards a distal end of the sheath.

13. The system as recited in claim 9, wherein each sidewall opening in the sheath has a pair of angled portions extending from an inner surface to an outer surface of the sheath, each anchor member moving along the pair of angled portions as the anchor member extends from the sheath.

14. The system of claim 9, wherein the anchor member is positioned proximal a distal end of the elongate member.

15. A system comprising:
an elongate member having an anchor member extending transversely from the elongate member, the anchor member having a rectangular cross-section, the rectangular cross-section having a dimension thicker in a direction along a length of the elongate member to resist bending in the longitudinal direction, a portion the anchor member curves at least partially around the elongate member within the sheath: and a sheath having a lumen, the sheath receiving the elongate member and selectively constraining movement of the anchor member in a direction transverse to a longitudinal axis of the sheath, the anchor member is biased to extend transversely outwardly with respect to the longitudinal axis of the sheath and through a closed perimeter, sidewall opening to a deployed configuration.

16. The system as recited in claim 15, wherein the anchor member is integrally formed with or fastened to the elongate member.

17. The system as recited in claim 15, wherein the anchor member comprises a shape-memory material.

18. The system of claim 15, wherein the anchor member is positioned proximal a distal end of the elongate member.

19. A method comprising:
positioning a sheath within a body, the sheath having a closed perimeter, sidewall opening and a longitudinal axis; and moving the sheath relative an elongate member disposed within the sheath, the elongated member including an anchor member extending radially from the elongate member, the anchor member having an upper surface disposed and movable within a plane transverse to the longitudinal axis, the anchor member having a rectangular cross-section, the rectangular cross-section having a dimension thicker in a direction along a length of the elongate member to resist bending in the longitudinal direction, wherein moving the sheath relative the elongate member allows the anchor member to extend radially outwardly from the elongate member in a direction transverse to the longitudinal direction, wherein moving the sheath comprises:
rotating the sheath and the elongate member in the same direction at different speeds,
rotating the sheath while maintaining the elongate member stationary, or
rotating the sheath and the elongate member in opposite directions.

20. The method as recited in claim 19, wherein moving the sheath comprises moving a distal end of the anchor member outwardly within the plane, through the sidewall opening, and into tissue.

21. The method as recited in claim 19, wherein the anchor member springs outwardly to a deployed configuration.

* * * * *